United States Patent

Imura

[11] Patent Number: 5,956,133
[45] Date of Patent: Sep. 21, 1999

[54] APPARATUS FOR MEASURING A REFLECTION CHARACTERISTIC

[75] Inventor: Kenji Imura, Toyohashi, Japan

[73] Assignee: Minolta Co., Ltd., Osaka, Japan

[21] Appl. No.: 09/179,607

[22] Filed: Oct. 27, 1998

[30] Foreign Application Priority Data

Dec. 26, 1997 [JP] Japan ................................ 9-360609
Aug. 4, 1998 [JP] Japan ................................ 10-220606

[51] Int. Cl.⁶ .................................................. G01N 21/47
[52] U.S. Cl. .......................... 356/236; 356/446; 250/228
[58] Field of Search .................................. 356/236, 319, 356/416, 418, 419, 323, 325, 326, 328, 405–408, 446–448; 250/227, 228; 359/707–711

[56] References Cited

U.S. PATENT DOCUMENTS

| | | | |
|---|---|---|---|
| 4,932,779 | 6/1990 | Keane | 250/228 |
| 5,369,481 | 11/1994 | Berg et al. | 250/228 |
| 5,384,641 | 1/1995 | Imura | 356/446 |
| 5,859,709 | 1/1999 | Imura | 356/236 |

FOREIGN PATENT DOCUMENTS 9-61243  3/1997  European Pat. Off. .

*Primary Examiner*—Hoa Q. Pham
*Attorney, Agent, or Firm*—McDermott, Will & Emery

[57] ABSTRACT

A reflection characteristic measuring apparatus is provided with a hollow integrating sphere. The integrating sphere is formed with four apertures: a sample aperture where a sample to be measured is placed; a first illumination aperture for allowing light to enter the sphere from a first illuminator; a second illumination aperture for allowing light to enter the sphere from a second illuminator; and a measurement aperture for allowing light to exit from the sphere. A photoreceptor receives light reflected from the sample that exits the measurement aperture. A reflection characteristic calculator is used to for calculating first and second reflection characteristics of the sample based on the light received by the photoreceptor. A corrector is used to correct the calculated first and second reflection characteristics.

14 Claims, 5 Drawing Sheets

APPARATUS FOR MEASURING A REFLECTION CHARACTERISTIC

This application is based on patent application Ser. No. 93-60609 and 10-220606 filed in Japan, the contents of which is hereby incorporated by reference.

BACKGROUND OF THE INVENTION

This invention relates to an apparatus for measuring a reflection characteristic of a sample using an integrating sphere, which may be adopted in a spectral color measuring device.

Generally, measurement of a reflection characteristic of a sample is greatly affected by a configuration of an illuminator and a light receiving device (hereinafter, referred to as "geometric configuration"). Accordingly, almost all reflection property measuring devices such as spectral color measuring devices employ any one of the following geometric configurations which are recommended by the International Commission on Illumination (CIE: Commission Internationale de l'Eclairage).

45/0: the illuminator is so arranged as to illuminate the sample surface with light incident upon the sample surface at 45°, and the light receiving device is so arranged as to receive light reflected from the sample surface at 90°;

0/45: the illuminator is so arranged as to illuminate the sample surface with light incident upon the sample surface at 90°, and the light receiving device is so arranged as to receive light reflected from the sample surface at 45°;

d/0: the illuminator is so arranged as to illuminate the sample surface with diffused light, and the light receiving device is so arranged as to receive light reflected from the sample surface at 90°; and 0/d: the illuminator is so arranged as to illuminate the sample surface with light incident upon the sample surface at 90°, and the light receiving device is so arranged as to receive diffused light.

Among the above configurations, d/8 type (combination of diffused-light-illuminator and +8°-inclined-light-receiving-device), a variation of the d/0 configuration, has been widely used because it can measure both a reflection characteristic of a specular component included reflection light (or SCI spectral reflection) and a reflection characteristic of a specular component excluded reflection light (or SCE spectral reflection). The SCI spectral reflection is unlikely to be influenced by the surface condition of the sample and hence has measurement stability, and the SCE spectral reflection is close to visual sense.

To measure a reflection characteristic of SCI spectral reflection (hereinafter, merely referred to as "SCI reflection characteristic") and a reflection characteristic of SCE spectral reflection (hereinafter, merely referred to as "SCE reflection characteristic") in the d/8 type geometric configuration, there has been primarily used an integrating sphere provided with a mechanically openable trap member in an inner wall thereof. The inner wall of the trap member functions as a light source for specular reflection, and the SCI reflection characteristic is measured by closing the trap member and the SCE reflection characteristic is measured by opening the trap member.

Japanese Unexamined Patent Publication No. 9-61743 discloses a reflection characteristic measuring apparatus provided with an integrating sphere in which two kinds of illumination light with different light distributions illuminate a sample to measure a reflection characteristic of a sample without a mechanical device such as a trap member.

FIGS. 5 and 6 are schematic construction diagrams of the reflection characteristic measuring apparatus in the above publication.

FIG. 5 shows light distribution in an integrating sphere 100 when a first illuminator 110 is driven to emit light. Assuming that the first illuminator 110 illuminates a sample 3 with illumination light $I_1$, indicated at $I_{1d}$, $I_{1d}'$ are diffuse illumination light on the sample 3 respectively before the integrating sphere 100 is deteriorated to some extent (i.e., there is no or less possibility of measurement error concerning the reflection characteristic of the sample 3, hereinafter, this state is referred to as "initial state of the integrating sphere") and after the integrating sphere 100 is deteriorated (where a measurement error is liable to occur). Indicated at $M_{1d}$, $M_{1d}'$ are diffuse illumination light incident on an incident end of an optical fiber 141 respectively before and after the integrating sphere 100 is deteriorated when it is assumed that the first illuminator 110 illuminates the incident end of the optical fiber 141 with illumination light $M_1$.

FIG. 6 shows light distribution in the integrating sphere 100 when a second illuminator 120 is driven to emit light. Assuming that the second illuminator 120 illuminates the sample 3 with illumination light $I_2$, indicated at $I_{2d}$, $I_{2d}'$ are diffuse illumination light on the sample 3 respectively before and after the integrating sphere 100 is deteriorated. Indicated at $M_{2d}$, $M_{2d}'$ are diffuse illumination light incident on the incident end of the optical fiber 141 respectively before and after the integrating sphere 100 is deteriorated when it is assumed that the second illuminator 120 illuminates the incident end with illumination light $M_2$.

Indicated at $I_{2s}$, $I_{2s}'$ are illumination components to be reflected specularly on the sample 3 as the light $I_{2d}$, $I_{2d}'$, hereinafter merely referred to as illumination components for specular reflection, and $M_{2s}$, $M_{2s}'$ are illumination components for specular reflection on the incident end as the light $M_d$, $M_{2d}'$, respectively before and after the integrating sphere 100 is deteriorated.

In this reflection characteristic measuring apparatus, it should be appreciated that the illumination light $I_1$ that illuminates the sample 3 and the monitor light $M_1$ that is incident on the incident end of the optical fiber 141 vary proportionally to each other. Likewise, the illumination light $I_2$ that illuminates the sample 3 and the monitor light $M_2$ that is incident on the incident end of the optical fiber 141 vary proportionally to each other.

The optical fiber 141 is connected to an unillustrated spectral device to indirectly monitor the illumination light $I_1$ by monitoring change of the monitor light $M_1$ and indirectly monitor the illumination light $I_2$ by monitoring change of the monitor light $M_2$. In other words, this measuring apparatus adopts the so-called "dual beam system". It should be appreciated that the measuring apparatus is so constructed as to satisfy the following equations: $I_1 = I_{1d}$, $M_1 = M_{1d}$, $I_2 = I_{2d} + I_{2s}$, $M_2 = M_{2d} + M_{2s}$.

In the above reflection characteristic measuring apparatus, the integrating sphere 100 is formed with a sample aperture 102 where the sample 3 to be measured is placed, illumination apertures 116, 126 respectively for allowing light to be incident from the first illuminator 110 and the second illuminator 120, and a reception aperture 131 for allowing reflected light from the sample 3 to be incident upon a receiving optical system 132. An inner wall 101a of the integrating sphere 100 is applied with a white diffuse reflection paint such as $BaSO_4$, having a high diffusion coefficient and a high reflection coefficient.

Light from a light source 111 of the first illuminator 110 first illuminates a first region 105 having the relatively large area in the inner wall 101a of the integrating sphere 100, undergoes a multiple reflection on the inner wall 101a, and illuminates the sample 3. On the other hand, light from a light source 121 of the second illuminator 120 first illuminates a second region 104 in the inner wall 101a of the integrating sphere 100. The second illuminator 120 illuminates the sample 3 principally at an incident direction (in this case, −8° direction) symmetrical to an optical axis of the receiving optical system 132 with respect to a normal axis 102a to a surface of the sample 3. .

To summarize the above, the first illuminator 110 substantially uniformly and diffusely illuminates the sample 3 and the incident end of the optical fiber 141, while the second illuminator 120 illuminating the sample 3 in such a manner that light radiated in the −8° direction with respect to the normal axis 102a is strong relative to the other directions. In other words, the first illuminator 110 and the second illuminator 120 illuminate the sample 3 and the incident end of the optical fiber 141 with different light distributions.

As shown in FIG. 5, when the first illuminator 110 is driven in the initial state of the integrating sphere 100, the first illuminator 110 illuminates the sample 3 with the light $l_{1d}$. Accordingly, a first reflection characteristic $r_1$ of the sample 3 when the first illuminator 110 is driven in the initial state of the integrating sphere 100 is obtained based on spectral data of the reflected light of $I_{1d}$ which is inputted to the receiving optical system 132 and a sample spectral device (not shown) and a data processor (not shown).

On the other hand, as shown in FIG. 6, when the second illuminator 120 is driven in the initial state of the integrating sphere 100, the second illuminator 120 illuminates the sample 3 with the light $I_{2d}$ and the light $I_{2s}$. Accordingly, a second reflection characteristic $r_2$ of the sample 3 when the second illuminator 120 is driven in the initial state of the integrating sphere 100 is obtained based on spectral data of the reflected light of $(I_{2d}+I_{2s})$ which is inputted to the receiving optical system 132 and the sample spectral device and the data processor.

The data processor applies a linear combination to the thus obtained first reflection characteristic $r_1$ and the second reflection characteristic $r_2$ in accordance with Equation (1) to obtain a SCI reflection characteristic $r_i$ and a SCE reflection characteristic $r_e$.

$$r_i = p_1 \cdot r_1 + p_2 \cdot r_2$$
$$r_e = q_1 \cdot r_1 + q_2 \cdot r_2$$
[Equation 1]

where $p_1$, $p_2$ are weighting factors used to obtain the SCI reflection characteristic $r_i$, and $q_1$, $q_2$ are weighting factors used to obtain the SCE reflection characteristic $r_e$, and hereinafter respectively referred to as "SCI weighting factors $P_1$, $P_2$" and "SCE weighting factors $q_1$, $q_2$".

In the above reflection characteristic measuring apparatus, calibration is performed to correct a measurement error due to a deteriorated state of the inner wall 101a resulting from smear of the inner wall 101a (or simply referred to as "deteriorated state of the integrating sphere") and other factors. This deterioration cannot be avoided as the apparatus is put into a long-time use despite an attempt to continue measurement with a high precision.

Generally, calibration is performed with the use of a white reference sample before measurement. Specifically, assuming that a reflection characteristic of the white reference sample in the initial state of the integrating sphere 100 is w (the value w is known), a reflection characteristic of the white reference sample measured when the integrating sphere 100 is deteriorated is w', and a reflection characteristic of an arbitrary sample (i.e., sample 3) other than the white reference sample measured when the integrating sphere 100 is deteriorated is r', a true reflection characteristic r of the sample 3 which is supposed to be obtained in the initial state of the integrating sphere 100 is calculated in accordance with Equation (2).

$$r = (w/w') \cdot r'$$
[Equation 2]

However, the measuring apparatus in the above publication cannot properly calibrate the second reflection characteristic of the sample 3 with the use of the white reference sample when the second illuminator 120 is activated in a deteriorated state of the integrating sphere 100 because of the following reasons.

First, described is a case that the first reflection characteristic of the sample 3 is calibrated when the first illuminator 110 is activated with reference to FIG. 5. A light ray $S_1$ incident on the receiving optical system 132 is a combination of diffused reflection components and specular reflection components of the illumination light $I_1$ which illuminates the sample 3. Assuming that a reflection characteristic of diffused reflection on the sample 3 is $r_d$, and a reflection characteristic of specular reflection on the sample 3 is $r_s$, the light ray $S_1$ can be expressed by Equation (3) because of $I_1 = I_{1d}$:

$$S_1 = K \cdot I_1(r_d + r_s)$$
$$= K \cdot I_{1d}(r_d + r_s)$$
[Equation 3]

where K is a ratio of light rays that are incident on the receiving optical system 132 to a total of light rays that are reflected in the hollow space of the integrating sphere 100, and is a constant which is determined according to a configuration of the integrating sphere and the receiving optical system 132.

Since $M_1 = M_{1d}$, the first reflection characteristic $r_1$ of the sample 3 is calculated in accordance with Equation (4).

$$r_1 = C_1 \cdot (S_1/M_1) \qquad \text{[Equation 4]}$$
$$= C_1 \cdot K \cdot I_{1d}(r_d + r_s)/M_{1d}$$

where $C_1$ is a proportional coefficient.

At this time, it is assumed that the light $I_{1d}$ and the light $M_{1d}$ decrease amounts of $a_s$, $a_m$ ($a_s$, $a_m \ll 1$) due to a deteriorated state of the integrating sphere 100, and change to light $I_{1d}'$ and light $M_{1d}'$, respectively. The light $I_{1d}'$ and the light $M_{1d}'$ are expressed by Equation (5).

$$I_{1d}' = I_{1d}(1-a_s) \qquad \text{[Equation 5]}$$
$$M_{1d}' = M_{1d}(1-a_m)$$

A first reflection characteristic $r_1'$ of the sample 3 which is measured when the first illuminator 110 is driven in a deteriorated state of the integrating sphere 100 is expressed by Equation (6).

$$r_1' = C_1 \cdot K \cdot I_{1d}'(r_d + r_s)/M_{1d}' \qquad \text{[Equation 6]}$$
$$= C_1 \cdot K \cdot I_{1d} \cdot (1-a_s)(r_d + r_s)/[M_{1d} \cdot (1-a_m)]$$
$$= r_1 \cdot (1-a_s)/(1-a_m)$$

Thus, Equation (7) is calculated based on Equation (6).

$$r_1 = A_1 \cdot r_1' \qquad \text{[Equation 7]}$$

where $A_1$ denotes a first correction coefficient, and is expressed as $A_1 = (1-a_m)/(1-a_s)$.

If the inner wall 101a of the integrating sphere 100 maintains the good diffusiveness, it can be assumed that $a_s \approx a_m$. Accordingly, $A_1 = (1-a_m)/(1-a_s) \approx 1$, and $r_1 \approx r_1'$.

On the other hand, in the case where $A_1$ 1, i.e., $r_1$ $r_1'$ due to a deteriorated state of the integrating sphere 100 or other causes, calibration is performed with the use of a white reference sample in accordance with Equation (2). The first correction coefficient $A_1$ is calculated by executing the equation: $A_1 = w_1/w_1'$ where $w_1$ is a reflection characteristic of the white reference sample that is obtained when the first illuminator 110 is driven in the initial state of the integrating sphere 100 and $w_1'$ is an observed reflection characteristic of the white reference sample that is obtained when the first illuminator 110 is driven in the deteriorated state of the integrating sphere 100. In this way, the first observed sample reflection characteristic $r_1'$ can be properly corrected.

Next, described is a case that the second illuminator 120 is activated with reference to FIG. 6. As mentioned above, when the second illuminator 120 is driven in the initial state of the integrating sphere 100, the sample 3 is illuminated with illumination light $I_2$ and the monitor light $M_2$ is incident on the incident end of the optical fiber 141. This state is expressed by Equation (8).

$$I_2 = I_{2d} + I_{2a} \qquad \text{[Equation 8]}$$
$$M_2 = M_{2d} + M_{2s}$$

Accordingly, light ray $S_2$ incident on the receiving optical system 132 are expressed by Equation (9). As shown in Equation (9), the light ray $S_2$ is a sum of the first term and the second term wherein the first term represents a combination of diffused reflection components and specular reflection components of the diffuse illumination light $I_{2d}$ and the second term represents a combination of diffused reflection components and specular reflection components of the illumination component for specular reflection $I_{2d}$. As mentioned above, $r_d$ is the diffused reflection characteristic of the sample 3, $r_s$ is the specular reflection characteristic of the sample 3, and K is the ratio of the light rays $S_2$ that is incident on the receiving optical system 132 to the total reflected rays that is radiated in the hollow space of the integrating sphere 100.

$$S_2 = K \cdot I_{2d}(r_d + r_s) + I_{2s}(K \cdot r + r_s) \qquad \text{[Equation 9]}$$

Accordingly, the second reflection characteristic $r_2$ is expressed by Equation (10).

$$r_2 = C_2 \cdot (S_2/M_2) \qquad \text{[Equation 10]}$$
$$= C_2 \cdot [K \cdot I_{2d}(r_d + r_s) + I_{2s}(K \cdot r_d + r_s)]/M_2$$

where $C_2$ is a proportional coefficient.

Assuming that the light $I_{2d}$ and the light $M_{2d}$ decrease an amount of $a_s$, $a_m$ ($a_s$, $a_n \ll 1$) due to a deteriorated state of the integrating sphere 100, and change to the light $I_{2d}'$ and the light $M_{2d}'$, respectively, the light $I_{2d}'$ and the light $M_{2d}'$ are expressed by Equation (11).

$$I_{2d}' = I_{2d}(1-a_s) \qquad \text{[Equation 11]}$$
$$M_{2d}' = M_{2d}(1-a_m)$$

At this time, after a multiple reflection on the inner wall 101a of the integrating sphere 100, the light $I_{2d}$ and the light $M_{2d}$ (diffuse illumination components) respectively in the illumination light $I_2$ and the monitor light $M_2$ illuminate the sample 3 and the incident end of the optical fiber 141. On the other hand, the light $I_{2s}$ and the light $M_{2s}$ (illumination components for specular reflection) respectively in the illumination light $I_2$ and the monitor light $M_2$ illuminate the sample 3 and the incident end after a single reflection on the specific region 104 of the inner wall 101a.

Accordingly, it can be said that the influence of deterioration of the inner wall of the integrating sphere 100 (i.e., lower in the reflection characteristic of the inner wall) is much smaller for the illumination component for specular reflection than for the diffused illumination component. Assuming that the lower in the reflection characteristic of the inner wall is negligible for the illumination component for specular reflection, the illumination light $I_2'$ and the monitor light $M_2'$ which vary from the initial illumination light $I_2$ and the initial monitor light $M_2$ as the integrating sphere 100 is getting deteriorated, are expressed by Equation (12).

$$I_2' \approx I_{2d}(1-a_s) + I_{2s} \qquad \text{[Equation 12]}$$
$$M_2' \approx M_{2d}(1-a_m) + M_{2s}$$

Accordingly, an observed second sample reflection characteristic $r_2'$ of the sample 3 which is measured in a deteriorated state of the integrating sphere 100 is expressed by Equation (13).

$$r_2' \approx C_2 \cdot (S_2'/M_2') \quad \text{[Equation 13]}$$
$$= C_2 \cdot [K \cdot I_{2d} \cdot (1-a_s)(r_d + r_s) + I_{2s}(K \cdot r_d + r_s)] / [M_{2d} \cdot (1-a_m) + M_{2s}]$$

As shown in Equations (10) and (13), the second true reflection characteristic $r_2$ and the second observed sample reflection characteristic $r_2'$ before and after the integrating sphere 100 is deteriorated cannot be expressed with a simple proportional relationship, whereas the first true reflection characteristic $r_1$ and the first observed sample reflection characteristic $r_1'$ before and after the integrating sphere 100 is deteriorated are expressed with a simple proportional relationship, as shown in Equation (7). Accordingly, the second observed reflection characteristic $r_2'$ of the sample 3 cannot be properly calibrated with the use of the white reference sample in accordance with Equation (2) because of the fact that the deteriorated state of the integrating sphere 100 gives different influences to the diffused illumination component and the illumination component for specular reflection as mentioned above.

Specifically, the light intensity of the diffused illumination component relative to the illumination component for specular reflection on the sample 3 and the incident end of the optical fiber 141 ($I_{2d}/I_{2s}$ of the illumination light $I_2$ and $M_{2d}/M_{2s}$ of the monitor light $M_2$) unavoidably changes when the second illuminator 120 is driven as the integrating sphere 100 is getting deteriorated.

However, in the reflection characteristic measuring apparatus disclosed in Japanese Unexamined Patent Publication No. 9-61243, the weighting factors $p_1$, $p_2$, $q_1$, $q_2$ in Equation (1) are set on the assumption that the above relative light intensities do not change.

In the case where the relative light intensity is changed to a non-negligible extent due to a deteriorated state of the integrating sphere 100, it is required to calculate the weighting factors again. Calculation of the weighting factors requires measurements of reflection characteristics of plurality of reference samples as mentioned in the publication. Further, it requires ample care to store these reference samples in a stable condition free from change of the reflection characteristic.

Accordingly, there has been demanded a simple calibration manner to correct a second observed sample reflection characteristic $r_2'$ after the integrating sphere is deteriorated which makes it possible to use weighting factors obtained before a deterioration of the integrating, sphere as the simple calibration for first sample reflection characteristic $r_1'$ using a white reference sample.

Further, there have to be considered other factors which may lead to a measurement error when measuring the first reflection characteristic and the second reflection characteristic using the first illuminator 110 and the second illuminator 120 besides deterioration of the integrating sphere 100, for example, deterioration of optical elements other than the integrating sphere 100, such as the receiving optical system 132, and changes in the ambient temperature and humidity. Accordingly, there has also been demanded a measure that can compensate the measurement error of the first reflection characteristic and the second reflection characteristic resulting from these factors.

SUMMARY OF THE INVENTION

It is an object of the present invention to provide a reflection characteristic measuring apparatus which has overcome the problems residing in the prior art.

According to an aspect of the invention, an apparatus for measuring a reflection characteristic, the apparatus comprises: an integrating sphere formed with a first illumination aperture, a second illumination aperture, a sample aperture, and a measurement aperture; a first illuminator which is disposed at the first illumination aperture, and projects light rays onto a first specified region of an inner wall of the integrating sphere to illuminate a sample placed in the sample aperture; a second illuminator which is disposed at the second illumination aperture, and projects light rays onto a second specified region of the inner wall of the integrating sphere to illuminate the sample, the second specified region being at a symmetrical position with the measurement aperture with respect to a normal axis to a surface of a the sample; a photoreceptor which is disposed at the measurement aperture, and receives light reflected from the sample to output light reception data corresponding to an intensity of received light; a controller which activates the first illuminator and the second illuminator individually, thereby permitting the photoreceptor to output first light reception data under activation of the first illuminator, and second light reception data under activation of the second illuminator; a reflection characteristic calculator which calculates a first reflection characteristic of the sample based on the first light reception data and a second reflection characteristic of the sample based on the second light reception data; a coefficient storage device which stores a proportional coefficient, a first correction coefficient, and a second correction coefficient, these coefficients being calculated based on a reference sample having a known reflection characteristic; and a corrector which corrects the calculated first and second reflection characteristics in the state of the apparatus at measurement that has a deterioration in accordance with the following equations into first and second reflection characteristics obtainable in an initial state of the apparatus that has no deterioration:

$r_1 = A_1 \cdot r_1'$
$r_2 = r_2' \cdot A_2 \, (r_2' - C \cdot r_1),$
$r_2 = r_2' \cdot A_2 \cdot (r_2' - C \cdot r_1'),$
$r_2 = A_1 \cdot \{r_2' - A_2 \cdot (r_2' - C \cdot r_1)\},$ or
$r_2 = A_1 \cdot \{r_2' - A_2 \cdot (r_2' - C \cdot r_1')\}$ wherein
 $r_1$: first reflection characteristic in the initial state,
 $r_2$: second reflection characteristic in the initial state,
 $A_1$: first correction coefficient,
 $A_2$: second correction coefficient,
 C: proportional coefficient,
 $r_1'$: first reflection characteristic in the state at measurement,
 $r_3'$: second reflection characteristic in the state at measurement.

These and other objects, features and advantages of the present invention will become more apparent upon reading of the following detailed description and accompanying drawings.

DETAILED DESCRIPTION OF THE PREFERRED EMBODIMENT OF THE INVENTION

Figure 1:
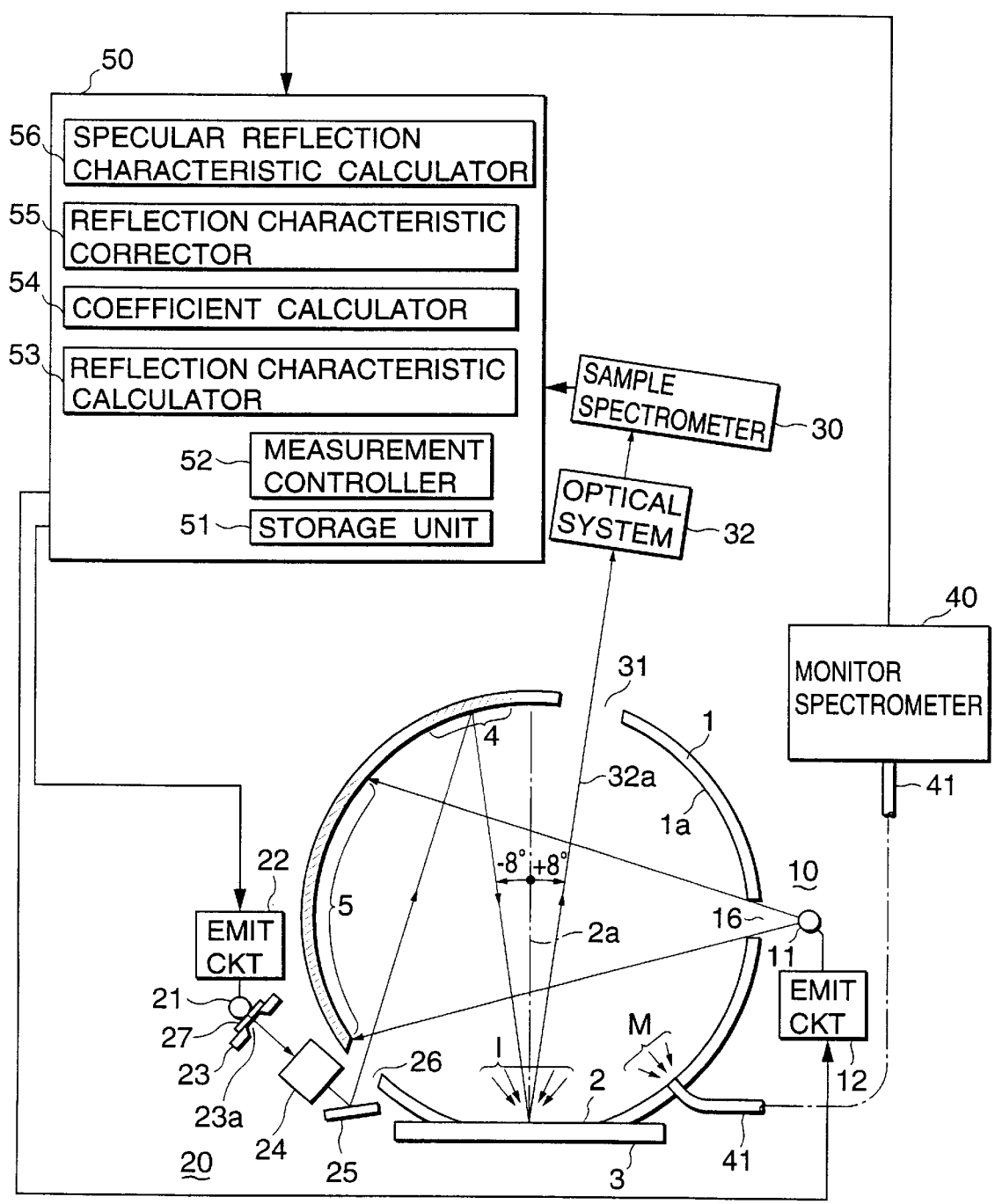
FIG. 1 is a diagram showing a construction of a reflection characteristic measuring apparatus embodying the present invention.

FIG. 1 shows a construction of a reflection characteristic measuring apparatus embodying the invention. This reflection characteristic measuring apparatus includes an integrating sphere 1. The integrating sphere 1 is a hollow sphere. An inner surface 1a of the integrating sphere 1 is applied with a white diffuse reflection material, such as MgO and BaSO$_4$, having a high diffusion coefficient and a high reflection coefficient.

The integrating sphere 1 is formed with a sample aperture 2 where a sample 3 to be measured is placed, a first illumination aperture 16 for allowing light to be incident from a light source 11 of a first illuminating system 10, a second illumination aperture 26 for allowing light to be incident from a light source 21 of a second illuminating system 20, and a measurement aperture 31 for allowing reflected light from the sample 3 to be incident upon a receiving optical system 32. The sample aperture 2 is formed in a bottom of the integrating sphere 1. The first light source aperture 16 is formed on the center ring of the integrating sphere 1. The second light source aperture 26 is formed in the left side of the sample aperture 2 in FIG. 1. The measurement aperture 31 is formed on an axis inclined by +8° with respect to a normal axis 2a to a surface of the sample 3.

The first illuminating system 10 includes the light source 11 disposed immediately behind the first illumination aperture 16 and an emitting circuit 12. A xenon flash lamp or the like is used as the light source 11 to supply light into the integrating sphere 1 so as to first illuminate a direct illuminating region (or first region) 5 with a relatively large area in the inner surface 1a. The emitting circuit 12 drives the light source 11 to emit light, and is controlled by a measurement controller 52 which is described later.

The second illuminating system 20 includes the light source 21, an emitting circuit 22, an illumination region restricting plate 23, an illuminating optical system 24, a reflector 25, and a light diffuse member 27. A xenon flash lamp or the like is used as the light source 21 to supply light into the integrating sphere 1. The emitting circuit 22 drives the light source 21 to emit light, and is also controlled by the measurement controller 52.

The light diffuse member 27 is disposed near the light source 21 and includes a translucent plate for diffusing the light from the light source 21. The restricting plate 23 has an aperture 23a and is adapted to restrict the illumination region of the light from the light source 21. The optical system 24 includes a lens, and is adapted to converge light passed through the aperture 23a on a direct illuminating region (or second region) 4 in the inner surface 1a via the reflector 25.

The second region 4 is located along a direction of −8° with respect to the normal axis 2a. The second illuminating system 20 is arranged to make the second region 4 and the measurement aperture 31 symmetrical with respect to the normal axis 2a.

The receiving optical system 32 includes a lens, and forms a d/8 optical system which is set such that an optical axis 32a is inclined by +8° with respect to the normal axis 2a to the surface of the sample 3. Hence, this optical system 32 receives a reflection light along the direction of +8° from the sample 3. The optical system 32 focuses the received reflection light on a sample spectrometer 30.

The sample spectrometer 30 receives the reflection light from the sample 3 to output spectral data corresponding to a spectral intensity of the reflected light. The spectral data is transmitted to a controller 50 which is described later.

In the above arrangement, when the light source 11 of the first illuminating system 10 is turned on, light is projected onto the first region 5 of the inner surface 1a of the integrating sphere 1. The first region 5 has a large area, and the projected light undergoes a multiple reflection on the inner surface 1a. Accordingly, the sample 3 is substantially uniformly and diffusely illuminated from every direction by the first illuminating system 10.

When the light source 21 of the second illuminating system 20 emits light, light rays, after having been improve the uniformity by the light diffuse member 27, pass through the aperture 23a of the restricting plate 23. Thereupon, the optical system 24 forms an image corresponding to the aperture 23a on the second region 4 of the inner wall 1a of the integrating sphere 1, thereby first illuminating the second region 4.

After reflected on the second region 4, the light also undergoes a multiple reflection. However, in addition to the diffused light generated by the multiple reflection, the reflected light from the second region 4 directly illuminates the sample 3, and light rays of specular reflection on the sample surface are incident on the light receiving system 32 through the measurement aperture 31. This means that the second illuminating system 20 resultantly illuminates the sample 3 with illumination light having such a light distribution that emphasizes a specular reflection in addition to the diffuse illumination light.

A light guide 41 is mounted on the integrating sphere 1. The light guide 41 includes an optical fiber or the like material, and introduces part of the illumination light in the integrating sphere 1, which is incident upon an incident end of the light guide 41, to a monitoring spectrometer 40.

Similar to the case of the sample 3, the first illuminating system 10 substantially uniformly and diffusely illuminates the incident end of the light guide 41, and the second illuminating system 20 illuminates the incident end with illumination light having such a light distribution that emphasizes a specular reflection at the sample 3 in addition to the diffuse illumination light.

The monitoring spectrometer 40 receives the illumination light introduced by the light guide 41 to output spectral data of the illumination light. The spectral data is transmitted to the controller 50 for monitoring the illumination light.

The controller 50 includes a CPU which centrally controls an operation of the reflection characteristic measuring apparatus. The controller 50 further comprises a storage unit 51, the measurement controller 52, a reflection characteristic calculator 53, a coefficient calculator 54, a reflection characteristic corrector 55, and a specular reflection characteristic calculator 56.

The storage unit 51 stores a control program for measurement, weighting factors set in advance such as SCI weighting factors $p_1$, $p_2$ and SCE weighting factors $q_1$, $q_2$, and first and second correction coefficients $A_1$, $A_2$ set in advance for correcting a measurement error due to deterioration of the integrating sphere 1, and temporarily stores the spectral data which is outputted from the sample spectrometer 30 and the monitoring spectrometer 40. The weighting factors are described later in detail.

The measurement controller 52 controls the emitting circuits 12, 22 to individually drive the light sources 11, 21 to emit light, and controls the sample spectrometer 30 and the monitoring spectrometer 40 to output spectral data of the light emitted from the light sources 11, 21.

The reflection characteristic calculator 53 calculates, according to a procedure which is described later, a first reflection characteristic of the sample 3 based on the spectral data of the reflection light from the sample 3 that is outputted from the sample spectrometer 30 and the spectral data of the monitor light that is outputted from the monitoring spectrometer 40 when the first illuminating system 10 is driven.

The reflection characteristic calculator 53 also calculates, according to a procedure which is described later, a second reflection characteristic of the sample 3 based on the spectral data of the reflection light from the sample 3 that is outputted from the sample spectrometer 30 and the spectral data of the monitor light that is outputted from the monitoring spectrometer 40 when the second illuminating system 20 is driven.

The coefficient calculator 54 performs the following operations ① to ⑤.

① The coefficient calculator 54 calculates coefficients $C_1$, $C_2$ using a white reference sample having a first reference reflection characteristic $w_1$ and a second reference reflection characteristic $w_2$ which are known, according to a procedure which is described later, and also executes the equation: $C = C_2/C_1$. The thus obtained proportional coefficient C is stored in the storage unit 51.

② A measurement value (first observed reference reflection characteristic) $w_1'$ is obtained by measuring the white reference sample having the known first reference reflection characteristic $w_1$. The first correction coefficient $A_1$ is calculated in accordance with Equation (14), which is obtained by transforming Equation (7) ($r_1 = +e$,crc A+hd 1+ee ·$r_1'$).

$$A_1 = r_1/r_1', \text{ i.e., } A_i = w_1 w_1' \quad \text{[Equation 14]}$$

③ As described later, the second correction coefficient $A_2$ is calculated in accordance with Equation (24) or (26) by measuring the white reference sample having the known first reference reflection characteristic $w_1$ and the known second reference reflection characteristic $w_2$.

④ The thus obtained first correction coefficient $A_1$ and the second correction coefficient $A_2$ are stored in the storage unit 51.

⑤ The SCI weighting factors $p_1$, $p_2$ and the SCE weighting factors $q_1$, $q_2$ are calculated in accordance with Equations (27), (28), (29), (30) that are described later, and the thus obtained weighting factors $p_1$, $p_2$, $q_1$, $q_2$ are stored in the storage unit 51.

The reflection characteristic corrector 55 corrects the first reflection characteristic in accordance with Equation (7) using the first correction coefficient $A_1$ stored in the storage unit 51, and corrects the second reflection characteristic in accordance with Equation (21) or (22) using the second correction coefficient $A_2$.

The specular reflection characteristic calculator 56 calculates the SCI reflection characteristic $r_i$ and the SCE reflection characteristic $r_c$ of the sample 3 in accordance with Equation (1) using the corrected first reflection characteristic, the corrected second reflection characteristic, the SCI weighting factors $p_1$, $p_2$, and the SCE weighting factors $q_1$, $q_2$.

Next, the principle of calculation of the second correction coefficient $A_2$ by the coefficient calculator 54 is described.

It could be presumed that when observing a change in the second reflection characteristic $r_2$ of the sample 3 under the driving of the second illuminating system 20, a measurement error due to a difference between the values $a_s$ and $a_m$ respectively representing a decreased amount of the light $I_{2d}$ and the light $M_{2d}$ after a deterioration of the integrating sphere 1 (see Equation (11)) is negligibly small, compared to a measurement error due to a difference between relative light intensities $I_{2d}/I_{2s}$ and $M_{2d}/M_{2s}$. Accordingly, the equation: $a_s = a_m = a$ can be established.

In this case, $M_2'$ of Equation (15) is calculated based on Equations (8) and (12), and $S_2'$ of Equation (15) is calculated based on Equations (9) and (12).

$$M_2' \approx M_{2d} - a_m \cdot M_{2d} + M_{2s} \quad \text{[Equation 15]}$$
$$= M_2(1 - a \cdot M_{d2}/M_2)$$

-continued
$$S_2' \approx K \cdot I_{2d}'(r_d + r_s) + I_{2s}(K \cdot r_d + r_s)$$
$$= K \cdot I_{2d}(1-a)(r_d + r_s) + I_{2s}(K \cdot r_d + r_s)$$
$$= S_2 - a \cdot K \cdot I_{2d}(r_d + r_s)$$

Equation (16) is obtained based on Equations (10) and (15).

$$r_2' \approx C_2 \cdot (S_2'/M_2') \quad \text{[Equation 16]}$$
$$= C_2 \cdot [S_2 - a \cdot K \cdot I_{2d}(r_d + r_s)]/[M_2(1 - a \cdot M_{2d}/M_2)]$$
$$\approx (C_2/M_2) \cdot (1 + a \cdot M_{2d}/M_2)[S_2 - a \cdot K \cdot I_{2d}(r_{2d} + r_s)]$$
$$\approx r_2 + r_2 \cdot a \cdot M_{2d}/M_2 - (C_2/M_2) \cdot a \cdot K \cdot I_{2d}(r_d + r_s)$$

Equation (17) is obtained by transforming Equation (4).

$$K \cdot (r_d + r_s) = (r_1 \cdot M_{1d})/(C_1 \cdot I_{1d}) \quad \text{[Equation 17]}$$

Substituting Equation (17) for Equation (16) obtains Equation (18).

$$r_2' \approx r_2 + r_2 \cdot a \cdot M_{2d}/M_2 - (C_2/C_1) \cdot a \cdot I_{2d} \cdot \quad \text{[Equation 18]}$$
$$(r_1 \cdot M_{1d})/(M_{2d} \cdot I_{1d})$$
$$= r_2 + r_2 \cdot a \cdot M_{2d}/M_2 - r_1 \cdot a \cdot (C_2/C_1)(M_{2d}/M_2) \cdot$$
$$(I_{2d}/M_{2d})(M_{1d}/I_{1d})$$

The light intensity of the diffused illumination component on the surface of the sample 3 relative to that at the incident end of the light guide 41 does not change depending on the illuminating system. Accordingly, Equation (19) is established.

$$I_{2d}/M_{2d} \approx I_{1d}/M_{1d} \quad \text{[Equation 19]}$$

Thus, Equation (20) is obtained based on Equations (18) and (19).

$$r_2' \approx r_2 + r_2 \cdot a \cdot M_{2d}/M_2 - r_1 \cdot a \cdot (C_2/C_1)(M_{2d}/M_2) \quad \text{[Equation 20]}$$
$$= r_2 + a \cdot M_{2d}/M_2[r_2 - r_1 \cdot (C_2/C_1)]$$

Substituting the equation: $C=C_2/C_1$, $A_2=a \cdot M_{2d}/M_2$ for Equation (20) obtains Equation (21).

$$r_2 \approx r_2' - A_2 \cdot (r_2 - C \cdot r_1) \quad \text{[Equation 21]}$$
$$\approx r_2' - A_2 \cdot (r_2' - C \cdot r_1)$$

In Equation (21), it is assumed that the second term is enough small compared to the first term that it can be considered that a serious error may not occur even if $r_2$ is replaced by $r_2'$.

It should be appreciated that Equation (22) may be used instead of Equation (21).

$$r_2 \approx r_2' - A_2 \cdot (r_2' - C \cdot r_1') \quad \text{[Equation 22]}$$

Similar to Equation (21), in Equation (22), it is assumed that the second term is enough small compared to the first term that it can be considered that a serious error may not occur even if $r_1$ is replaced by $r_1'$.

As expressed by Equation (21) or (22), the second observed reflection characteristic $r_2'$ obtained when the second illuminating system 20 is driven in a deteriorated state of the integrating sphere 1 can be corrected to the second reflection characteristic $r_2$ which is expected to be obtained in the initial state of the integrating sphere 1 according to the following procedure. The correction is performed based on the second correction coefficient $A_2$ and the proportional coefficient $C(=C_2/C_1)$ where $C_1$ denotes the coefficient that makes the reflection characteristic $r_1$ proportional to the ratio $S_1/M_1$ (ratio of the light incident on the sample spectrometer 30 to that incident on the monitoring spectrometer 40 in the initial state of the integrating sphere 1) and $C_2$ denotes the coefficient that makes the reflection characteristic $r_2$ proportional to the ratio $S_2/M_2$ (ratio of the light incident on the sample spectrometer 30 to that incident on the monitoring spectrometer 40 after deterioration of the integrating sphere 1) (see Equations (4) and (10)).

It should be appreciated that the first observed reflection characteristic $r_1'$ be corrected prior to the second observed reflection characteristic $r_2'$ in the case where Equation (21) is used.

Specifically, transforming Equation (21) obtains Equation (23).

$$A_2 \approx (r_2' - r_2)/(r_2' - C \cdot r_1) \quad \text{[Equation 23]}$$

Assuming that $w_1$ and $w_2$ are respectively the known first reference reflection characteristic and the known second reference reflection characteristic of the white reference sample in the initial state of the integrating sphere 1, and $w_1'$ and $w_2'$ are respectively the first observed reference reflection characteristic and the second observed reference reflection characteristic of the white reference sample measured after deterioration of the integrating sphere 1, the second correction coefficient $A_2$ is calculated in accordance with Equation (24).

$$A_2 \approx (w_2' - w_2)/(w_2' - C \cdot w_1) \quad \text{[Equation 24]}$$

Further, transforming Equation (22) obtains Equation (25).

$$A_2 \approx (r_2' - r_2)/(r_2' - C \cdot r_1') \quad \text{[Equation 25]}$$

In this case, the second correction coefficient $A_2$ may be obtained in accordance with Equation (26).

$$A_2 \approx (w_2' - w_2)/(w_2' - C \cdot w_2') \quad \text{[Equation 26]}$$

Next, described is the principle of calculating the SCI weighting factors $p_1$, $p_2$ and the SCE weighting factors $q_1$, $q_2$ by the coefficient calculator 54.

This principle is basically the same as that disclosed in Japanese Unexamined Patent Publication No. 9-61243. Specifically, the weighting factors can be calculated by measuring two different kinds of reference sample having known different SCI and SCE reflection characteristics, e.g., different surface states.

Let it be assumed that reference samples Sa and Sb are measured, and the SCI reflection characteristic and the SCE reflection characteristic of the reference sample Sa are respectively $Ra_1$ and $Ra_e$, and the SCI reflection characteristic and the SCE reflection characteristic of the reference sample Sb are respectively $Rb_i$ and $Rb_e$, where $Ra_i$ $Rb_i$, $Ra_e$ $Rb_e$.

The reference sample Sa is disposed in the sample aperture 2, and the first illuminating system 10 and the second illuminating system 20 are individually driven to obtain a first observed reflection characteristic $ra_1$ and a second observed reflection characteristic $ra_2$.

The reference sample Sb is disposed in the sample aperture 2, and the first illuminating system 10 and the second illuminating system 20 are individually driven to obtain a first observed reflection characteristic $rb_1$ and a second observed reflection characteristic $rb_2$.

The following Equations (27), (28), (29), and (30) are established.

$$Ra_i = p_1 \cdot ra_1 + p_2 \cdot ra_2 \quad \text{[Equation 27]}$$

$$Rb_i = p_1 \cdot rb_1 + p_2 \cdot rb_2 \quad \text{[Equation 28]}$$

$$Ra_e = q_1 \cdot ra_1 + q_2 \cdot ra_2 \quad \text{[Equation 29]}$$

$$Rb_e = q_1 \cdot rb_1 + q_2 \cdot rb_2 \quad \text{[Equation 30]}$$

Solving Equations (27) and (28) obtains the SCI weighting factors $p_1$, $p_2$, and solving Equations (29) and (30) obtains the SCE weighting factors $q_1$, $q_2$. These weighting factors $p_1$, $p_2$, $q_1$, $q_2$ are values inherent to the measuring apparatus. Accordingly, the weighting factors are obtained in the initial stage of the integrating sphere 1.

Next, an operation procedure of the reflection characteristic measuring apparatus is described with reference to FIGS. 2 to 4.

Figure 2:
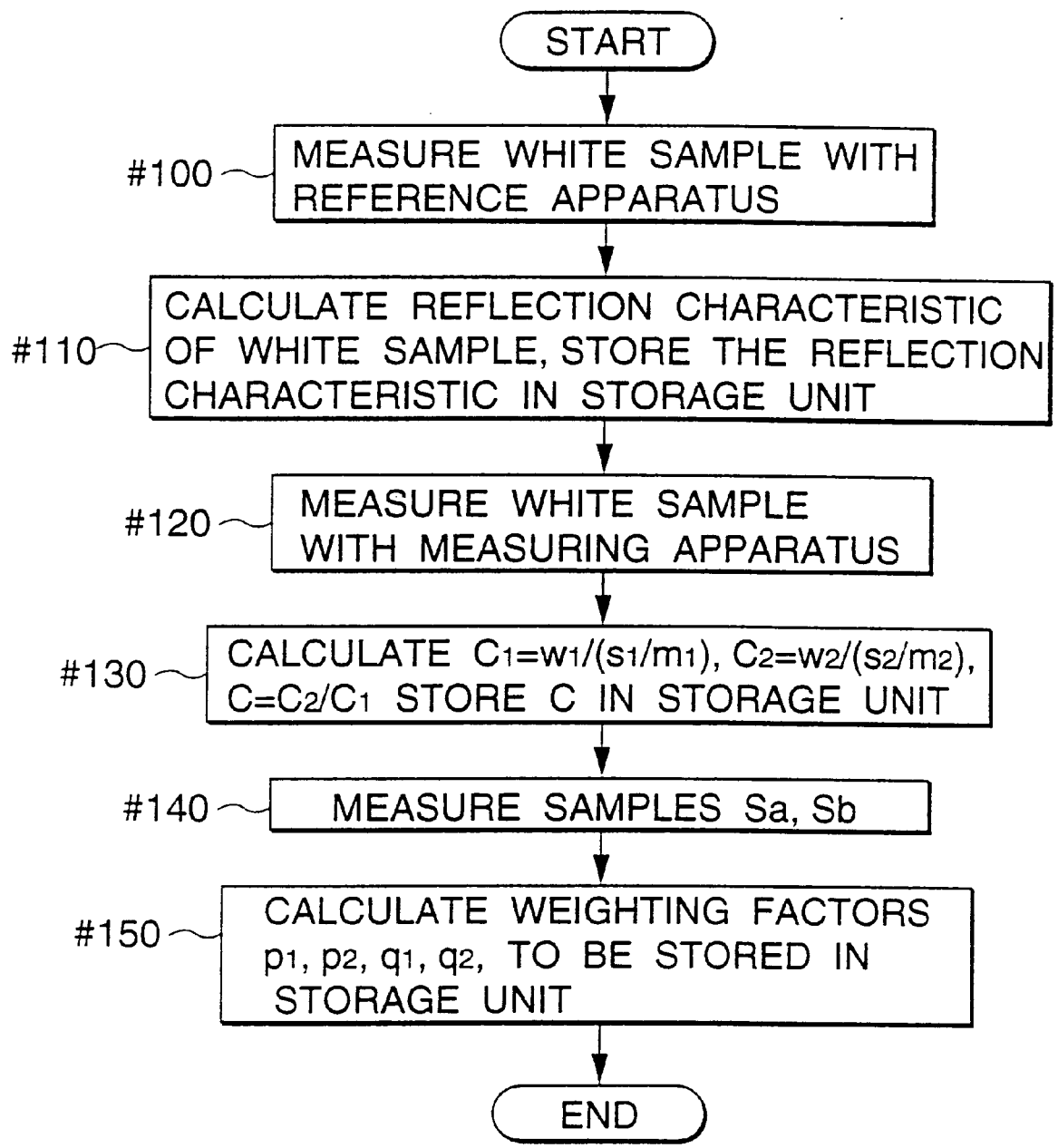
FIG. 2 is a flowchart showing a calibration procedure in a manufacturing factory which produces the reflection characteristic measuring apparatus.

FIG. 2 is a flowchart showing a calibration procedure in a manufacturing factory which produces the reflection characteristic measuring apparatus.

First, prepared is a reference measuring apparatus which is the same type as a reflection characteristic measuring apparatus of this embodiment to be marketed (hereinafter, referred to as "measuring apparatus App-X") and which has already been calibrated. A white reference sample Samp-X that is to be supplied together with the measuring apparatus App-X for calibration is disposed in a sample aperture of the prepared reference measuring apparatus. The first illuminating system 10 and the second illuminating system 20 are individually driven to generate spectral data which are in turn stored in the storage unit 51 of the measuring apparatus App-X (in Step #100).

Next, a first reference reflection characteristic $w_1$ and a second reference reflection characteristic $w_2$ of the white reference sample Samp-X are calculated based on the respective spectral data stored in the storage unit 51, and the thus obtained reflection characteristics $w_1$ and $w_2$ are stored in the storage unit 51 (in Step #110).

Subsequently, the white reference sample Samp-X is disposed in the sample aperture 2 of the measuring apparatus App-X, and the first illuminating system 10 and the second illuminating system 20 are individually driven to generate first spectral data $s_1$ and second spectral data $s_2$ that are generated respectively based on a reflection light ray $S_1$ and a reflection light ray $S_2$ from the white reference sample Samp-X, and first spectral data $m_1$ and second spectral data $m_2$ that are generated respectively based on monitor light $M_1$ and monitor light $M_2$ incident on the incident end of the light guide 41 and to store these spectral data $s_1$, $s_2$, $m_1$, $m_2$ in the storage unit 51 (in Step #120).

Next, coefficients $C_1 = w_1/(s_1/m_1)$, $C_2 = w_2/(s_2/m_2)$ are calculated based on the spectral data $s_1$, $s_2$, $m_1$, $m_2$ to calculate $C = C_2/C_1$, and the thus obtained proportional coefficient C is stored in the storage unit 51 (in Step #130).

Subsequently, reference samples having different reflection characteristics, e.g., reference samples Sa and Sb are disposed in the sample aperture 2 of the measuring apparatus App-X one by one, and the first illuminating system 10 and the second illuminating system 20 are individually driven to generate respective spectral data so as to store them in the storage unit 51 (in Step #140). The weighting factors $p_1$, $p_2$, $q_1$, $q_2$ are calculated in accordance with Equations (27), (28), (29), (30) and these calculated weighting factors $p_1$, $p_2$, $q_1$, $q_2$ are stored in the storage unit 51 (in Step #150), and this routine ends.

It should be appreciated that all the data generated in this routine are data obtained in an initial state of the integrating sphere 1.

Figure 3:
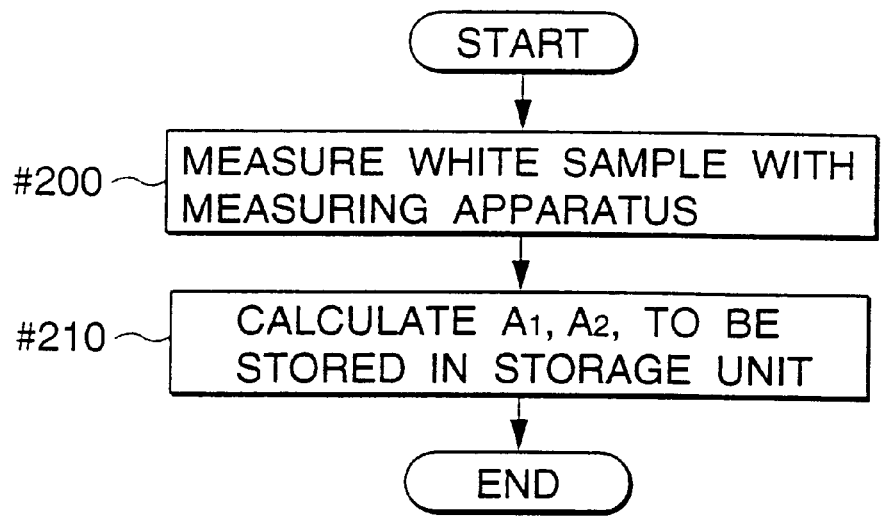
FIG. 3 is a flowchart showing a calibration procedure in a measurement site prior to an actual measurement of a sample using the reflection characteristic measuring apparatus.

FIG. 3 is a flowchart showing a calibration procedure in a measuring site prior to an actual sample measurement using the measuring apparatus App-X.

Prior to an actual measurement of a reflection characteristic of a sample 3 with the use of the measuring apparatus App-X, in the measuring site, the white reference sample Samp-X having the first and second reference reflection characteristics $w_1$ and $w_2$ given in the prior routine is disposed in the sample aperture 2 of the measuring apparatus App-X. The first illuminating system 10 and the second illuminating system 20 are individually driven to generate first spectral data concerning the first illuminating system 10 and second spectral data concerning the second illuminating system 20 to obtain a first observed reference reflection characteristic $w_1'$ and a second observed reference reflection characteristic $w_2'$ (in Step #200).

It should be considered a possibility that the calculated first observed reference reflection characteristic $w_1'$ and the calculated second observed reference reflection characteristic $w_2'$ have included a measurement error due to deterioration of the integrating sphere 1 of the measuring apparatus App-X. Accordingly, the first correction coefficient $A_1$ is calculated in accordance with Equation (14), the second correction coefficient $A_2$ is calculated in accordance with Equation (24) or (26) using the proportional coefficient C stored in the storage unit 51, and the calculated first and second correction coefficients $A_1$ and $A_2$ are stored in the storage unit 51 (in Step #210). Then, this routine ends.

Figure 4:
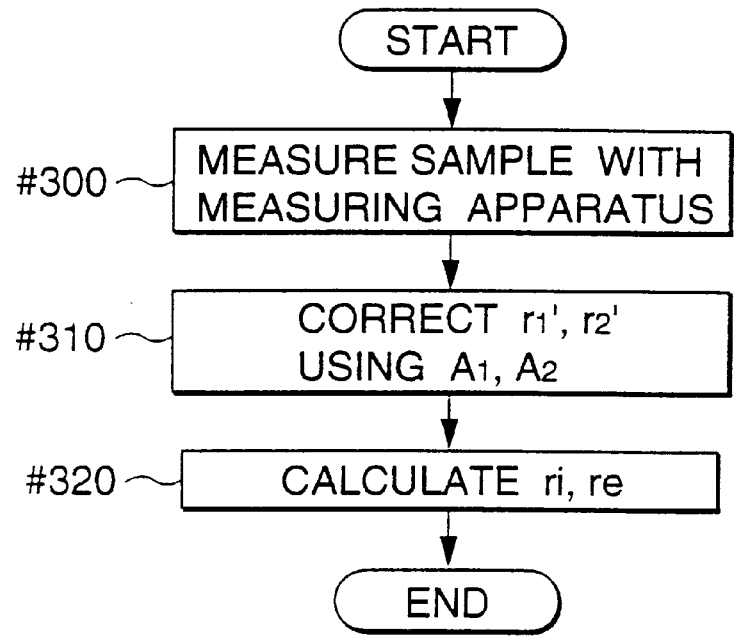
FIG. 4 is a flowchart showing a measurement procedure for measuring a sample using the reflection characteristic measuring apparatus.
Figure 5:
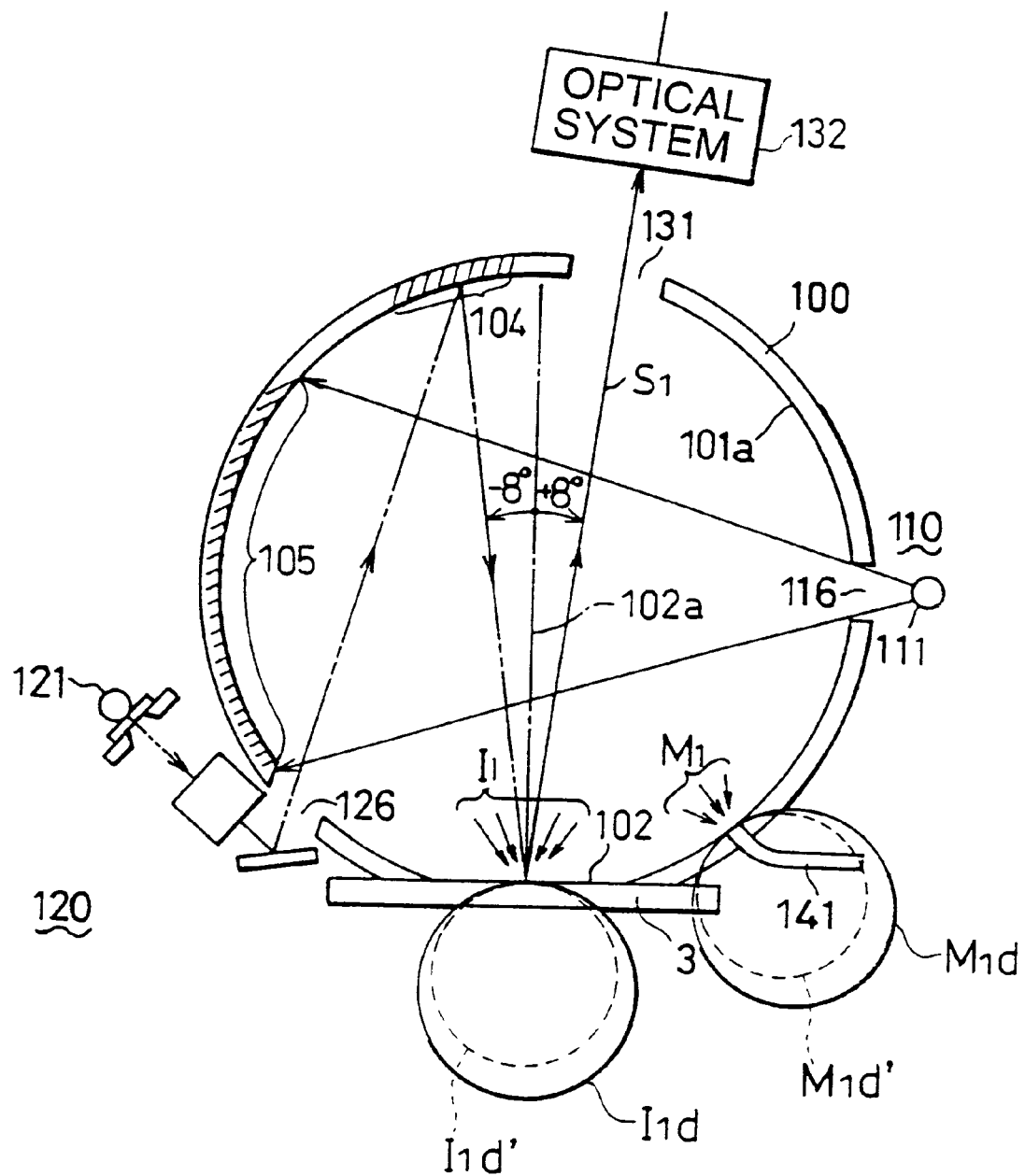
FIG. 5 is a schematic construction diagram of a reflection characteristic measuring apparatus, showing a variation of light distribution of illumination light on a sample surface and monitor light incident upon an incident end of a light guide before and after a deterioration of an integrating sphere when a first illuminator is driven.
Figure 6:
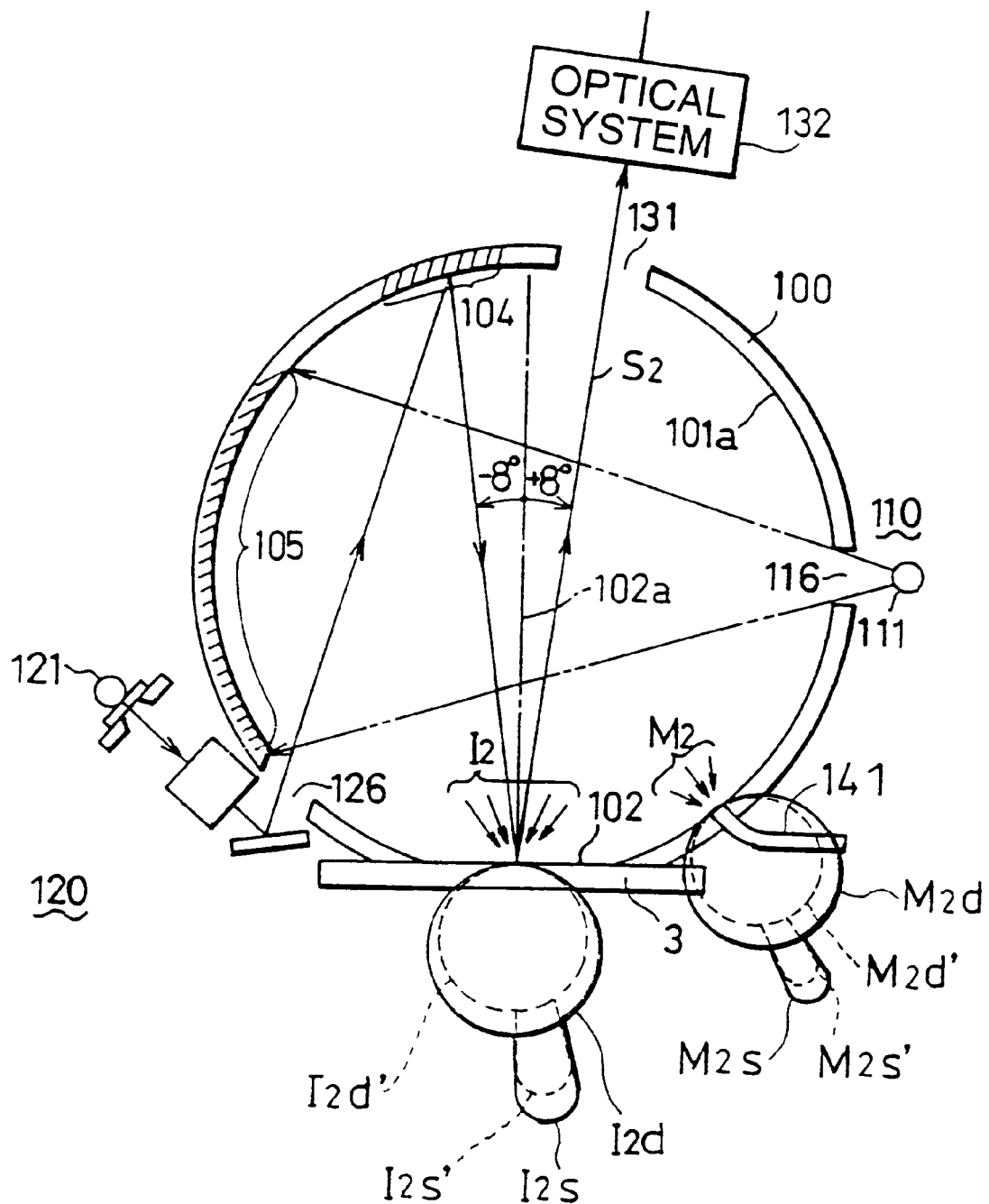
FIG. 6 is a schematic construction diagram of the conventional reflection characteristic measuring apparatus, showing a variation of light distribution of illumination light on the sample surface and monitor light incident upon the incident end of the light guide before and after deterioration of the integrating sphere when a second illuminator is driven.

FIG. 4 is a flowchart showing a measurement procedure for measuring the sample 3 using the measuring apparatus App-X.

The sample 3 is disposed in the sample aperture 2 of the measuring apparatus App-X, and the first illuminating system 10 and the second illuminating system 20 are individually driven, and a first observed reflection characteristic $r_1'$ of the sample 3 and a second observed reflection characteristic $r_2'$ of the sample 3 are calculated based on respective spectral data generated when the first illuminating system 10 and the second illuminating system 20 are driven (in Step #300).

At this time, also, it should be considered a possibility that the calculated first observed reflection characteristic $r_1'$ and the calculated second observed reflection characteristic $r_2'$ have included a measurement error due to deterioration of the integrating sphere 1 of the measuring apparatus App-X. Accordingly, the first observed reflection characteristic $r_1'$ is corrected to a value approximate to the first true reflection characteristic $r_1$, that is supposed to be obtained in the initial stage of the integrating sphere 1, in accordance with Equation (7) using the first correction coefficient $A_1$ stored in the storage unit 51, and the second observed refllectance $r_2'$ is corrected to a value approximate to the second true reflection characteristic $r_2$, that is supposed to be obtained in the initial stage of the integrating sphere 1, in accordance with Equation (21) or (22) using the second correction coefficient $A_2$ stored in the storage unit 51 (in Step #310).

Subsequently, the SCI reflection characteristic $r_i$ of the sample 3 is calculated in accordance with Equation (1) using the SCI weighting factors $p_1$, $p_2$ that are stored in the storage unit 51, and the SCE reflection characteristic $r_c$ of the sample 3 is calculated in accordance with Equation (1) using the SCE weighting factors $q_1$, $q_2$ that are stored in the storage unit 51 (in Step #320). Then, this routine ends.

As mentioned above, the white reference sample having the known first reference reflection characteristic $w_1$ and the known second reference reflection characteristic $w_2$ is measured in a deteriorated state of the integrating sphere 1 to obtain the first observed reference reflection characteristic $w_1'$ and the second observed reference reflection characteristic $w_2'$. The correction coefficient $A_1$ is calculated in accordance with Equation (14). The second correction coefficient $A_2$ is calculated in accordance with Equation (24) or (26) using the proportional coefficient C. The second observed reflection characteristic $r_2'$ is corrected to the second true reflection characteristic $r_2$ of the sample 3 using the second correction coefficient $A_2$. This can prevent a measurement error due to deterioration of the integrating sphere 1 accompanied by long-time use of the measuring apparatus (e.g., unavoidable decrease of the reflection characteristic of the inner wall of the integrating sphere 1), and accurate measurement can be maintained for a longer time.

In addition, the SCI reflection characteristic $r_i$ and the SCE reflection characteristic $r_c$ of the sample 3 are calculated using the SCI weighting factors $p_1$, $p_2$, SCE weighting factors $q_1$, $q_2$, the corrected first reflection characteristic that is approximate to the first true reflection characteristic $r_1$, and the corrected second reflection characteristic that is approximate to the second true reflection characteristic $r_2$. Thereby, calculation of the SCI reflection characteristic $r_i$ and the SCE reflection characteristic $r_c$ with a high precision can be maintained for a longer time.

Next, described is a modification of the reflection characteristic measuring apparatus.

It should be appreciated that an arrangement of the modified apparatus is substantially the same as that of the foregoing embodiment except the function and the operation of the coefficient calculator 54 and the reflection characteristic corrector 55. Accordingly, throughout the description of the modified apparatus, mainly described is a difference between the foregoing embodiment and the modification, and an operation of the modified apparatus focusing on the difference.

As mentioned in the BACKGROUND OF THE INVENTION section, there may be other causes for a measurement error of the first reflection characteristic and the second reflection characteristic of the sample 3 besides deterioration of an integrating sphere, such as deterioration of other elements, e.g., a receiving optical system and a light guide (optical fiber) as the measuring apparatus is placed in a long-time use, and a change in the ambient temperature and/or humidity.

When a light receiving efficiency of the receiving optical system 32 of the light guide 41 is changed, the first correction coefficient $A_1$ becomes $A_1$ 1. Even in this case, the first observed reflection characteristic $r_1'$ can be corrected in accordance with Equation (7) using the first correction coefficient $A_1$ that is obtained by executing Equation (14).

As mentioned in the BACKGROUND OF THE INVENTION section, as far as the inner wall of the integrating sphere 1 maintains the good diffusiveness (i.e., $a_s \approx a_m$) although it is deteriorated, the first correction coefficient $A_1$ becomes $A_1 \approx 1$. On the other hand, it can be assumed that factors other than the deterioration of the integrating sphere result the first correction coefficient $A_1$ 1 which affects the first reflection characteristic $r_1$ and the second reflection characteristic $r_2$ in a similar manner. Accordingly, the second observed reflection characteristic $r_2'$ can be corrected in accordance with Equation (31) in place of Equation (21).

$$r_2 \approx A_1 \cdot \{r_2' - A_2 \cdot (r_2 - C \cdot r_1)\} \qquad \text{[Equation 31]}$$
$$\approx A_1 \cdot \{r_2' - A_2 \cdot (r_2' - C \cdot r_1)\}$$

Alternatively, Equation (32) may be used in place of Equation (31), similar to the alternative case of the embodiment where Equation (22) is applied in place of Equation (21).

$$r_2 \approx A_1 \cdot \{r_2' - A_2 \cdot (r_2' - C \cdot r_1')\} \qquad \text{[Equation 32]}$$

Transforming Equation (31) obtains Equation (33).

$$A_2 \approx (r_2' - r_2/A_1)/(r_2' - C \cdot r_1) \qquad \text{[Equation 33]}$$

Accordingly, the second correction coefficient $A_2$ can be calculated in accordance with Equation (34) in place of Equation (24).

$$A_2 \approx (w_2' - w_2/A_1)/(w_2' - C \cdot w_1) \qquad \text{[Equation 34]}$$

Transforming Equation (32) obtains Equation (35).

$$A_2 \approx (r_2' - r_2/A_1)r_2' - C \cdot r_1') \qquad \text{[Equation 35]}$$

Accordingly, the second correction coefficient $A_2$ may be calculated in accordance with Equation (36).

$$A_2=(w_2'-w_2/A_1)/(w_2'-C\cdot w_1') \quad \text{[Equation 36]}$$

Next, an operation of the modified apparatus is described. In this modification, an operation similar to the flowcharts in FIGS. 3 and 4 is performed except steps corresponding to Steps #210 in FIG. 3 and Step #310 in FIG. 4. Specifically, in the step corresponding to Step #210, the second correction coefficient $A_2$ is calculated in accordance with Equation (34) (or Equation (36)) in place of Equation (24) (or Equation (26)). In the step corresponding to Step #310, the second observed reflection characteristic $r_2'$ is corrected to the value approximate to the second true reflection characteristic $r_2$ in accordance with Equation (31) (or Equation (32)) in place of Equation (21) (or Equation (22)).

In the foregoing embodiment, a measurement error due to factors other than the deterioration of the integrating sphere 1 is not considered. However, in the modification, the other factors are considered as well as the deterioration of the integrating sphere 1. Accordingly, a measurement error due to deterioration of the integrating sphere 1 and the other factors can be easily and optimally corrected similar to the foregoing embodiment.

In the embodiment and the modification, the white reference sample having the known first reference reflection characteristic $w_1$ and the known second reference reflection characteristic $w_2$ is used. The reference sample is not limited to the one shown in the above. For instance, a reference sample having the known first reflection characteristic and the known second reflection characteristic in a certain wavelength range may be used. In such a case, a reflection characteristic of a given sample in the certain wavelength range can also be corrected similar to the foregoing embodiment and the modification.

Further, in the foregoing embodiment and the modification, two reference samples are measured to obtain the weighting factors $p_1$, $p_2$, $q_1$, $q_2$ in accordance with simultaneous equations (i.e., the SCI weighting factors $p_1$, $p_2$ are calculated in accordance with Equations (27), (28), and the SCE weighting factor $q_1$, $q_2$ are calculated in accordance with Equations (29), (30)). Alternatively, reference samples of three or more kinds may be measured to calculate optimum weighting factors $p_1$, $p_2$, $q_1$, $q_2$ in accordance with the least-square method.

In the foregoina embodiment, the SCI reflection characteristic $r_s$ is calculated as a simple linear combination of the first reflection characteristic $r_1$ and the second reflection characteristic $r_2$ in which the SCI weighting factors $p_1$, $p_2$ respectively multiply the first reflection characteristic $r_1$ and the second reflection characteristic $r_2$ (see Equation (1)). Likewise, the SCE reflection characteristic $r_e$ is calculated as a simple linear combination of the first reflection characteristic $r_1$ and the second reflection characteristic $r_2$ in which the SCE weighting factors $q_1$, $q_2$ respectively multiply the first reflection characteristic $r_1$ and the second reflection characteristic $r_2$ (see Equation (1)). Alternatively, the square or the cubic of the first reflection characteristic r, and the second reflection characteristic $r_2$ may be multiplied by respective corresponding weighting factors and subject to a linear combination to obtain the SCI reflection characteristic $r_i$ (SCE reflection characteristic $r_e$).

In sum, a first true reflection characteristic $r_1$ and a second true reflection characteristic $r_2$ which are supposed to be obtained in an initial state of the integrating sphere are calculated based on a first observed reflection characteristic $r_1'$ and a second observed reflection characteristic $r_2'$ which are obtained in a deteriorated state of the integrating sphere in accordance with the following equation.

$$r_1=A_1\cdot r_1' \; r_2=r_2'-A_2\cdot(r_2'-C\cdot r_1) \text{ or } r_2=r_2'-A_2\cdot(r_2'-C\cdot r_1')$$

where $r_1$: first true reflection characteristic,
$r_2$: second true reflection characteristic,
$A_1$: the first correction coefficient,
$A_2$: second correction coefficient,
C: ratio of $C_2/C_1$,
$r_1'$: first observed reflection characteristic, and
$r_2'$: second observed reflection characteristic.

Execution of the above calculation prevents a measurement error of the reflection characteristic of a sample due to deterioration of the integrating sphere, and enables continued measurement of a reflection characteristic with high precision. Accordingly, the performance of the reflection characteristic measuring apparatus is remarkably improved.

The thus calculated proportional coefficient C, first correction coefficient $A_1$, and second correction coefficient $A_2$ using a reference sample enables calculation of a first true reflection characteristic $r_1$ and a second true reflection characteristic $r_2$ with high precision and ease.

A first true reflection characteristic $r_1$ and a second true reflection characteristic $r_2$ are calculated based on a first observed reflection characteristic $r_1'$ and a second observed reflection characteristic $r_2'$ in accordance with the following equation.

$r_1=A_1\cdot r_1'$
$r_2=A_1\cdot\{r_2'-A_2\cdot(r_2'-C\cdot r)\}$
or $r_2=A_1\{r_2'-A_2\cdot(r_2'-C\cdot r_1')\}$
where
$r_1$: first true reflection characteristic,
$r_2$: second true reflection characteristic,
$A_1$: first correction coefficient,
$A_2$: second correction coefficient,
C: proportional coefficient,
$r_1'$: first observed reflection characteristic, and
$r_2'$: second observed reflection characteristic.

Execution of the above calculation prevents an error in the measurement of a reflection characteristic of a sample due to deterioration of the integrating sphere and other factors, and enables continued measurement of a reflection characteristic with high precision. Accordingly, the durability of the reflection characteristic measuring apparatus is remarkably improved.

An SCI reflection characteristic $r_i$ and an SCE reflection characteristic $r_e$ are calculated based on a first reflection characteristic $r_1$ and a second reflection characteristic $r_2$. Accordingly, precise measurement of SCI reflection characteristic $r_i$ and SCE reflection characteristic $r_e$ can be maintained for a longer time.

The integrating sphere has a measurement aperture substantially formed in +8° direction with respect to the normal axis to the surface of a sample and a receiving optical system receives reflection light from the sample directed in the +8° direction. Accordingly, this arrangement is optimally applied to a widely-used reflection characteristic measuring apparatus with a geometric configuration of d/8 type (combination of diffused-illumination and +8° -inclined-observation), and the reflection characteristic of the sample can be measured with high precision.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. An apparatus for measuring a reflection characteristic, comprising:

an integrating sphere formed with a first illumination aperture, a second illumination aperture, a sample aperture, and a measurement aperture;

a first illuminator which is disposed at the first illumination aperture, and projects light rays onto a first specified region of an inner wall of the integrating sphere to illuminate a sample placed in the sample aperture;

a second illuminator which is disposed at the second illumination aperture, and projects light rays onto a second specified region of the inner wall of the integrating sphere to illuminate the sample, the second specified region being at a symmetrical position with the measurement aperture with respect to a normal axis to a surface of the sample;

a photoreceptor which is disposed at the measurement aperture, and receives light reflected from the sample to output light reception data corresponding to an intensity of received light;

a controller which activates the first illuminator and the second illuminator individually, thereby permitting the photoreceptor to output first light reception data under activation of the first illuminator, and second light reception data under activation of the second illuminator;

a reflection characteristic calculator which calculates a first reflection characteristic of the sample based on the first light reception data and a second reflection characteristic of the sample based on the second light reception data;

a coefficient storage device which stores a proportional coefficient, a first correction coefficient, and a second correction coefficient, these coefficients being calculated based on a reference sample having a known reflection characteristic; and a corrector which corrects the calculated first and second reflection characteristics in a state of the apparatus at measurement that has a deterioration in accordance with the following equations into first and second reflection characteristics obtainable in an initial state of the apparatus that has no deterioration:

$r_1 = A_1 \cdot r_1'$ $r_2 = r_2' - A_2 \cdot (r_2' - C \cdot r_1)$ or $r_2 = r_2' - A_2 \cdot (r_2' - C \cdot r_1')$ wherein $r_1$: first reflection characteristic in the initial state,
   $r_2$: second reflection characteristic in the initial state,
   $A_1$: first correction coefficient,
   $A_2$: second correction coefficient,
   C: proportional coefficient,
   $r_1'$: first reflection characteristic in the state at measurement,
   $r_2'$: second reflection characteristic in the state at measurement.

2. An apparatus according to claim 1, further comprising a coefficient calculator which calculates a proportional coefficient, a first correction coefficient, and a second correction coefficient, wherein:

the controller activates the first illuminator and the second illuminator in the initial state and the state at measurement respectively with the reference sample being placed in the sample aperture, thereby permitting the photoreceptor to output first reference light reception data under activation of the first illuminator and second reference light reception data under activation of the second illuminator in the initial state, and first reference light reception data under activation of the first illuminator and second reference light reception data under activation of the second illuminator in the state at measurement;

the reflection characteristic calculator calculates first and second reference reflection characteristics of the reference sample in the initial state based on the first and second reference light reception data in the initial state, and first and second reference reflection characteristics of the reference sample in the state at measurement based on the first and second reference light reception data in the state at measurement; and the coefficient calculator calculates the proportional coefficient based on the first and second reference light reception data in the initial state, and the first and second correction coefficients based on the first and second reference reflection characteristics in both the initial state and the state at measurement.

3. An apparatus according to claim 2, further comprising a specular reflection characteristic calculator which calculates a reflection characteristic of reflection light including a specular component and a reflection characteristic of reflection light excluding a specular component based on the first and second reflection characteristic in the initial state.

4. An apparatus according to claim 2, wherein the measurement aperture is substantially formed in 8° direction with respect to the normal axis to the surface of the sample, and the photoreceptor receives light rays reflected in the 8° direction from the sample.

5. An apparatus according to claim 1, further comprising a specular reflection characteristic calculator which calculates a reflection characteristic of reflection light including a specular component and a reflection characteristic of reflection light excluding a specular component based on the first and second reflection characteristic in the initial state.

6. An apparatus according to claim 5, wherein the measurement aperture is substantially formed in 8° direction with respect to the normal axis to the surface of the sample, and the photoreceptor receives light rays reflected in the 8° direction from the sample.

7. An apparatus according to claim 1, wherein the measurement aperture is substantially formed in 8° direction with respect to the normal axis to the surface of the sample, and the photoreceptor receives light rays reflected in the 8° direction from the sample.

8. An apparatus for measuring a reflection characteristic, comprising:

an integrating sphere formed with a first illumination aperture, a second illumination aperture, a sample aperture, and a measurement aperture;

a first illuminator which is disposed at the first illumination aperture, and projects light rays onto a first specified region of an inner wall of the integrating sphere to illuminate a sample placed in the sample aperture;

a second illuminator which is disposed at the second illumination aperture, and projects light rays onto a second specified region of the inner wall of the integrating sphere to illuminate the sample, the second specified region being at a symmetrical position with the measurement aperture with respect to a normal axis to a surface of the sample;

a photoreceptor which is disposed at the measurement aperture, and receives light reflected from the sample to output light reception data corresponding to an intensity of received light;

a controller which activates the first illuminator and the second illuminator individually, thereby permitting the photoreceptor to output first light reception data under activation of the first illuminator, and second light reception data under activation of the second illuminator;

a reflection characteristic calculator which calculates a first reflection characteristic of the sample based on the first light reception data and a second reflection characteristic of the sample based on the second light reception data;

a coefficient storage device which stores a proportional coefficient, a first correction coefficient, and a second correction coefficient, these coefficients being calculated based on a reference sample having a known reflection characteristic; and a corrector which corrects the calculated first and second reflection characteristics in a state of the apparatus at measurement that has a deterioration in accordance with the following equations into first and second reflection characteristics obtainable in an initial state of the apparatus that has no deterioration:

$r_1 = A_1 \cdot r_1'$ $r_2 = A_1 \cdot \{r_2' - A_2 \cdot (r_2' - C \cdot r_1)\}$ or $r_2 = A_1 \cdot \{r_2' - A_2 \cdot (r_3' - C \cdot r_1')\}$ wherein $r_1$: first reflection characteristic in the initial state, $r_2$: second reflection characteristic in the initial state, $A_1$: first correction coefficient, $A_2$: second correction coefficient, C: proportional coefficient, $r_1'$: first reflection characteristic in the state at measurement, $r_2'$: second reflection characteristic in the state at measurement.

9. An apparatus according to claim 8, further comprising a coefficient calculator which calculates a proportional coefficient, a first correction coefficient, and a second correction coefficient, wherein:

the controller activates the first illuminator and the second illuminator in the initial state and the state at measurement respectively with the reference sample being placed in the sample aperture, thereby permitting the photoreceptor to output first reference light reception data under activation of the first illuminator and second reference light reception data under activation of the second illuminator in the initial state, and first reference light reception data under activation of the first illuminator and second reference light reception data under activation of the second illuminator in the state at measurement;

the reflection characteristic calculator calculates first and second reference reflection characteristics of the reference sample in the initial state based on the first and second reference light reception data in the initial state, and first and second reference reflection characteristics of the reference sample in the state at measurement based on the first and second reference light reception data in the state at measurement; and the coefficient calculator calculates the proportional coefficient based on the first and second reference light reception data in the initial state, and the first and second correction coefficients based on the first and second reference reflection characteristics in both the initial state and the state at measurement.

10. An apparatus according to claim 9, further comprising a specular reflection characteristic calculator which calculates a reflection characteristic of reflection light including a specular component and a reflection characteristic of reflection light excluding a specular component based on the first and second reflection characteristic in the initial state.

11. An apparatus according to claim 9, wherein the measurement aperture is substantially formed in 8° direction with respect to the normal axis to the surface of the sample, and the photoreceptor receives light rays reflected in the 8° direction from the sample.

12. An apparatus according to claim 8, further comprising a specular reflection characteristic calculator which calculates a reflection characteristic of reflection light including a specular component and a reflection characteristic of reflection light excluding a specular component based on the first and second reflection characteristic in the initial state.

13. An apparatus according to claim 12, wherein the measurement aperture is substantially formed in 8° direction with respect to the normal axis to the surface of the sample, and the photoreceptor receives light rays reflected in the 8° direction from the sample.

14. An apparatus according to claim 8, wherein the measurement aperture is substantially formed in 8° direction with respect to the normal axis to the surface of the sample, and the photoreceptor receives light rays reflected in the 8° direction from the sample.

* * * * *

UNITED STATES PATENT AND TRADEMARK OFFICE
CERTIFICATE OF CORRECTION

PATENT NO.  : 5,956,133
DATED       : September 21, 1999
INVENTOR    : Imura

It is certified that error appears in the above-identified patent and that said Letter Patent is hereby corrected as shown below:

Column 23,

Claim 8, line 45, change "$r_3'$" to --$r_2'$--.

Signed and Sealed this

Twenty-fifth Day of April, 2000

Q. TODD DICKINSON

Attest:

Attesting Officer

Director of Patents and Trademarks